US00PP11134P

United States Patent [19]

Stemkens

[11] Patent Number: Plant 11,134

[45] Date of Patent: Nov. 30, 1999

[54] VERBENA PLANT NAMED 'CHARMENA'

[75] Inventor: Henricus G. W. Stemkens, Hoorn, Netherlands

[73] Assignee: Novartis Seeds B.V., Enkhuizen, Netherlands

[21] Appl. No.: 08/994,670

[22] Filed: Dec. 19, 1997

[51] Int. Cl.[6] ..... A01H 5/00

[52] U.S. Cl. ..... Plt./308

[58] Field of Search ..... Plt./87, 308

[56] References Cited

PUBLICATIONS

Hortus Third: A Concise Dictionary of Plants Cultivated in the United States and Canada. Bailey et al. MacMillan Pub. New York. pp. 1209–1210, 1976.

Peter Walton, Principles and Practices of Plant Science. pp. 29–30, 1988.

UPOV ROM, 1998/01, Plant Variety Database, GTI Jouve Retrieval Software, citation for 'Charmena', Oct. 1996.

*Primary Examiner*—Howard J. Locker
*Assistant Examiner*—Anne Marie Grüberg
*Attorney, Agent, or Firm*—Thomas Hoxie

[57] ABSTRACT

A new Verbena plant particularly distinguished by its large cherry-red flower, early flowering, and a vigorous spreading plant habit.

2 Drawing Sheets

BACKGROUND OF THE NEW PLANT

The present invention comprises a new distinct cultivar of Verbena, botanically known as *Verbena×hybrida*. The new cultivar is propagated from cuttings resulting from the cross of W801 and V514. W801 is a Deep Red flowering Verbena having a spreading habit. W801 is not commercially available and is not known by any synonyms. V514 is a Scarlet flowering Verbena having a semi-erect habit. V514 is not commercially available and is not known by any synonyms. Neither W801 or V514 has been patented. As a result of this cross the present cultivar was created in 1995 in Enkhuizen, Netherlands and has been repeatedly asexually reproduced by cuttings in Enkhuizen, Netherlands and Sarrians, France over a two year period. It has been found to retain its distinctive characteristics through successive propagations, and this novelty appears to be firmly fixed.

DESCRIPTION OF THE NEW CULTIVAR

The following detailed descriptions set forth the distinctive characteristics of this new Verbena. The data which defines these characteristics were collected from asexual reproductions carried out in Enkhuizen, Netherlands. The plant history was taken on plants that were 18 weeks old, blossomed under natural light in a greenhouse. Color readings were taken in the greenhouse under ambient light. Color references are primarily to the R.H.S. Color Chart of The Royal Horticultural Society of London.

DESCRIPTION OF THE DRAWING

This new Verbena plant is illustrated by the accompanying photographic drawings which show blooms, buds and foliage of the plant in full color, the color shown being as true as can be reasonably obtained by conventional photographic procedures.

THE PLANT

Figure 1:
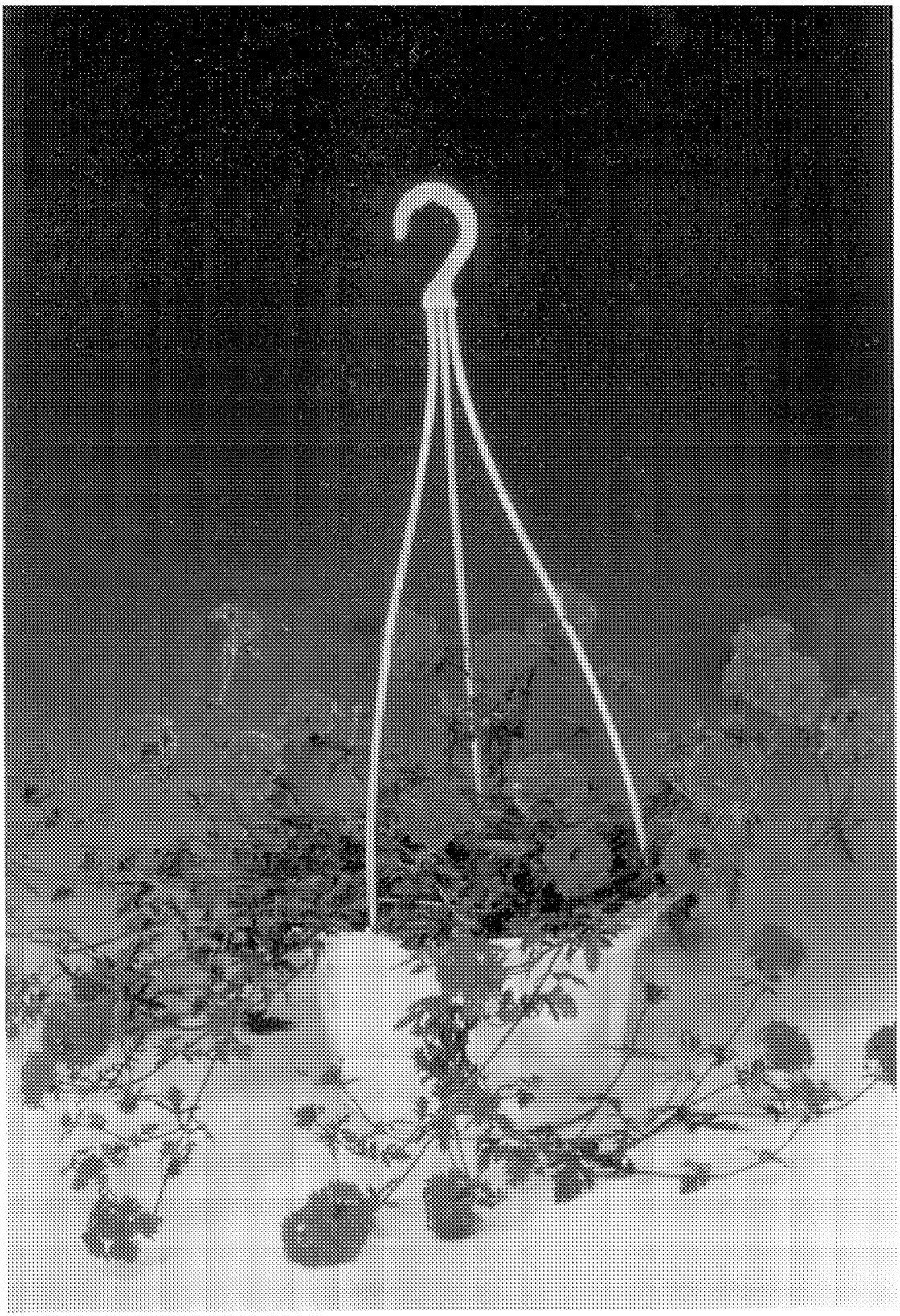
FIG. 1 depicts the spreading and hanging habit of the mature plant, while FIG. 2 provides a more detailed depiction of the blooms and foliage.
Figure 2:
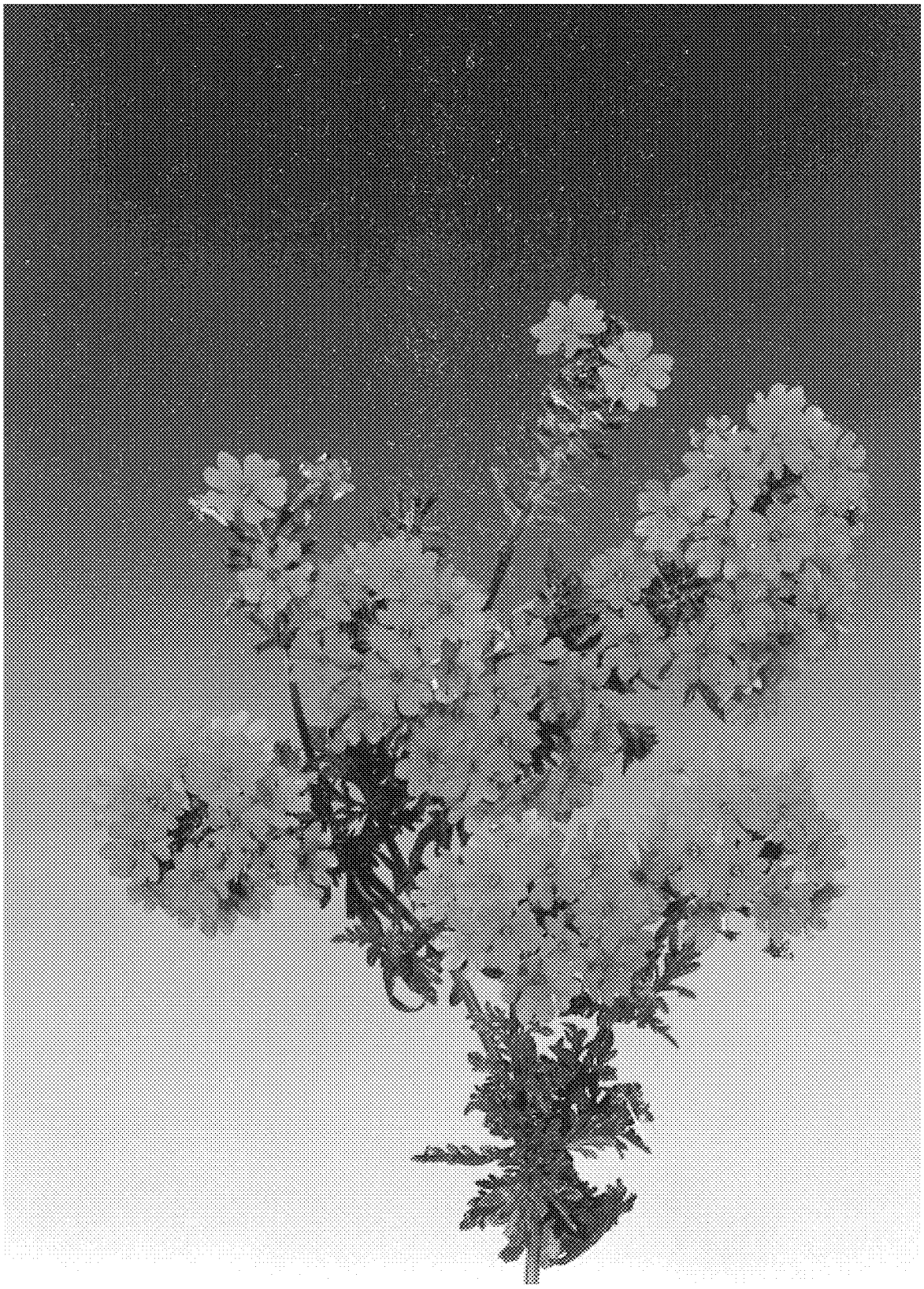

Classification:
*Botanical.*—Verbena×hybrida.
Parentage:
*Female parent.*—A seedling named W801 is one of our seedlings from our W-generation of plants bred in 1994.
*Pollen parent.*—A seedling named V514 is one of our seedlings from our V-generation of plants bred in 1993.
Growth habit: Spreading.
Plant height: 15–25 cm.
Spreading area of plant: 80–120 cm.
Strength: Very good.
Branching character: After pinching 6–8 breaks occur.
Blooming period: From April until November.

THE STEM

Diameter: 1.5–2 mm.
Cross section: Tetragonal.
Anthocyan pigmentation: Absent.
Length of internode: 30–80 mm, depending on the light where the plant is grown. Under high light condition, the length is shorter; under dark conditions, length is longer.
Pubescence: Strong pubescence.

THE FOLIAGE

Phyllotaxis Opposite.
Shape of blade: Cleft to parted.
Length: 25–40 mm.
Width: 18–28 mm.
Depth of incision: 5–15 mm.
Number of incisions: Few (3–6) incisions per leaf.
Color:
*Upper side.*—Medium green 137A.
*Lower side.*—Light green 139B.
Pubescence: Some pubescence is present on both sides of the leaf.
Length of petiole: 10–15 mm.
Color of petiole: Medium green 137A.

THE BUD

Peduncle length: 50–100 mm, depending on season.
Size:
*Diameter.*—2 mm.
*Length.*—8–12 mm.
Shape: Long.
Color: Medium green 141B.
Sepals:
*Colour.*—Green 137C.
*Form.*—Upright.

THE FLOWER

Direction: Ascending.
Diameter: 16–18 mm.
Height: 16–18 mm.
Borne: In a cluster.
Form: Flat and symmetrical.
Cluster: Corymb.
Color: Upper Surface: Cherry-red 53B, later 53D; Lower surface: Cherry-rose 54A.
Eye: No eye.
Overlapping of petals: Separate.
Corymb:
*Length.*—20–40 mm.
*Diameter.*—30–40 mm.
Calyx: Length of 10–12 mm.
Anthocyan pigmentation of calyx limb: Absent.
Flowers in bloom at one time: Maximum 18
Duration of flowering:
*Flower.*—4–6 days.
*Inflorescence.*—14–21 days.
Fragrance: A very soft rosy-sweet fragrance.
Reproductive organs: 1 pistil, 5 stamens. Stamens not fertile, no seedset.
Physiological and ecological characteristics: Strong resistance to pets and diseases, particularly powdery mildew.

We claim:

1. A new and distinct variety of Verbena plant, substantially as herein illustrated and described, characterized particularly as to novelty by large cherry-red blooms, early flowering, and a growing habit that is spreading and hanging.

* * * * *